(12) United States Patent
Otsuka et al.

(10) Patent No.: US 7,189,246 B2
(45) Date of Patent: Mar. 13, 2007

(54) MEDICAL INSTRUMENT HOLDING DEVICE (75) Inventors: Satoshi Otsuka, Mitaka (JP); Masaaki Ueda, Sagamihara (JP)

(73) Assignee: Olympus Corporation, Tokyo (JP)

( * ) Notice: Subject to any disclaimer, the term of this patent is extended or adjusted under 35 U.S.C. 154(b) by 217 days.

(21) Appl. No.: 10/758,646

(22) Filed: Jan. 14, 2004

(65) Prior Publication Data

US 2004/0172012 A1    Sep. 2, 2004

(30) Foreign Application Priority Data

Jan. 15, 2003   (JP) .............................. 2003-007216

(51) Int. Cl.
*A61B 19/00* (2006.01)
*A61B 1/04* (2006.01)
(52) U.S. Cl. ..................... 606/130; 600/102
(58) Field of Classification Search ............... 248/121; 606/1; 600/102
See application file for complete search history.

(56) References Cited

U.S. PATENT DOCUMENTS

| 4,101,779 | A | * | 7/1978 | Schmedemann ............ 248/157 |
|---|---|---|---|---|
| 4,344,595 | A | * | 8/1982 | Heller et al. ................ 248/542 |
| 4,491,435 | A | * | 1/1985 | Meier .......................... 403/55 |
| 4,548,373 | A | * | 10/1985 | Komura .................... 248/122.1 |
| 4,742,825 | A | * | 5/1988 | Freund et al. .............. 606/158 |
| 4,863,133 | A | | 9/1989 | Bonnell |
| 4,867,405 | A | * | 9/1989 | Nakamura ............. 248/281.11 |
| 5,170,790 | A | | 12/1992 | Lacoste et al. |
| 5,288,043 | A | * | 2/1994 | Tigliev ................... 248/123.11 |
| 5,332,181 | A | * | 7/1994 | Schweizer et al. ...... 248/123.11 |
| 5,571,072 | A | * | 11/1996 | Kronner ..................... 600/102 |
| 5,597,146 | A | * | 1/1997 | Putman .................... 248/276.1 |
| 5,609,565 | A | | 3/1997 | Nakamura |
| 5,667,186 | A | * | 9/1997 | Luber et al. ................ 248/550 |
| 5,697,939 | A | | 12/1997 | Kubota et al. |
| 5,825,536 | A | * | 10/1998 | Yasunaga et al. ........... 359/384 |
| 5,857,492 | A | * | 1/1999 | Salamun ................... 137/636.1 |
| 5,918,844 | A | | 7/1999 | Ognier |
| 6,045,104 | A | * | 4/2000 | Nakamura et al. ...... 248/280.11 |
| 6,050,530 | A | * | 4/2000 | Nakamura ................ 248/123.2 |
| 6,079,681 | A | * | 6/2000 | Stern et al. ............... 248/278.1 |
| 6,306,146 | B1 | * | 10/2001 | Dinkler ....................... 606/130 |

(Continued)

FOREIGN PATENT DOCUMENTS

JP        6-113997       4/1994

(Continued)

*Primary Examiner*—Henry M. Johnson, III
(74) *Attorney, Agent, or Firm*—Scully, Scott, Murphy & Presser, P.C.

(57) ABSTRACT

A medical instrument holding device includes a grasping portion onto which a medical instrument is mounted, an acceptant arm supported by a link mechanism, and a ball joint element adapted to be fixed to and released from the acceptant arm. The grasping portion is connected to the acceptant arm by the ball joint element arranged above or below the longitudinal axis of the acceptant arm. A total weight of the grasping portion is always balanced so as to apply to the acceptant arm (ball joint element) so that an operator can move the grasping portion under the condition that no total weight is applied to the operator.

17 Claims, 5 Drawing Sheets

U.S. PATENT DOCUMENTS

| | | | |
|---|---|---|---|
| 6,471,165 B2 * | 10/2002 | Twisselmann | 248/123.11 |
| 6,491,273 B2 * | 12/2002 | King et al. | 248/276.1 |
| 6,514,239 B2 | 2/2003 | Shimmura et al. | |
| 6,569,084 B1 * | 5/2003 | Mizuno et al. | 600/102 |
| 6,575,653 B1 * | 6/2003 | Krauter | 403/55 |
| 6,899,307 B2 * | 5/2005 | Strauss et al. | 248/280.11 |
| 2002/0014567 A1 * | 2/2002 | King et al. | 248/276.1 |
| 2003/0230698 A1 * | 12/2003 | Strauss et al. | 348/648 |

FOREIGN PATENT DOCUMENTS

| | | |
|---|---|---|
| JP | 8-52158 | 2/1996 |
| JP | 2001-258903 | 9/2001 |
| WO | WO 95/10985 | 4/1995 |

* cited by examiner

MEDICAL INSTRUMENT HOLDING DEVICE

CROSS-REFERENCE TO RELATED APPLICATIONS

This application is based upon and claims the benefit of priority from the prior Japanese Patent Application No. 2003-007216, filed Jan. 15, 2003, the entire contents of which are incorporated herein by reference.

BACKGROUND OF THE INVENTION

1. Field of the Invention

The present invention relates to a medical instrument holding device for holding a treating device, endoscope or the like used in surgical operation.

2. Description of the Related Art

In recent years, in the field of surgical operation a variety of medical instruments such as observation devices and treating devices are increasingly being used for surgical operation. For example, an endoscope is used to observe the rear side of an operation site that an operator could not see directly by means of a microscope for operation. Moreover, supersonic waves are often used in inspections for confirming the internal structure of tissue scheduled to be surgically incised.

In the surgical operation, in general, a patient is laid on an operating table, and an operator positions by the side of the patient to carry out required surgical treatment in the operation site of the patient. In this case, a lumen provided at the surface of the patient by surgical incision has a spatial peculiarity that the longitudinal direction of the "hole" of the lumen substantially coincides with the direction of the gravity. Such a relation between the lumen and the gravity is necessarily realized from the arrangement between the patient and the operator.

As the surgical operation is proceeding in such a positional relation, a situation can occur that the operator must hold the medical instrument for a long period of time. In order to preclude this undesirable though possible situation, a wide variety of holding devices have been proposed to reduce operator's burden. For example, a holding device having a plurality of arms connected by articulations is typical. In this device, either of fixed and release conditions of the articulations can be selected by operation of an operator. After the operator has moved a medical instrument to a desired position under the released condition, he brings it into the fixed condition and makes the holding device support the medical instrument at the desired position.

As such a medical instrument holding device, for example, Jpn. Pat. Appln. KOKAI Publication No. 8-052158, U.S. Pat. No. 4,863,133, U.S. Pat. No. 5,170,790 and WO 95/10985 disclose devices using ball joint elements at articulations to realize a miniaturization of device, respectively.

In Jpn. Pat. Appln. KOKAI Publication No. 6-113997 proposed by the applicant of the present application, a medical instrument holding device with a counter balancing system is disclosed. According to this holding device, even when an arm is under a released condition, by balancing the weight of a medical instrument itself held by the device and another weight, the medical instrument can be held without any burden applying to an operator. Therefore, it is possible for the operator to disregard the weight of the medical instrument and to do its movement.

Figures 13A, 13B:
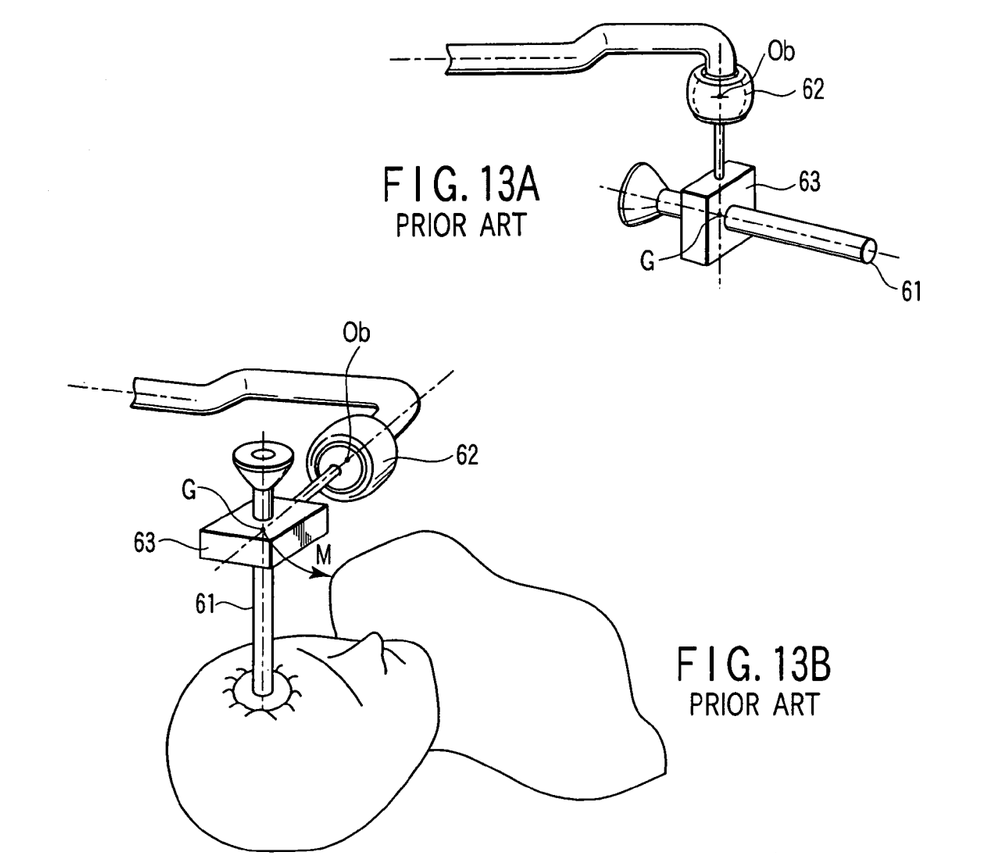
FIG. 13A is a view illustrating the outline of the endoscope holding portion of the medical instrument holding device of the prior art.
FIG. 13B is a view of a state using the endoscope holding portion of the medical instrument holding device of the prior art obliquely viewed from above.

Moreover, Jpn. Pat. Appln. KOKAI Publication No. 2001-258903 discloses a holding device employing a counter balancing system with links and using a ball joint element at one moving portion arranged at leading end of an arm. In this device, the leading end of the arm to be positioned in the proximity of an operating position is miniaturized by a ball joint element. As shown in FIG. 13A of the disclosed Application, further when the insertion shaft of an endoscope 61 is substantially horizontal, a balance can be ensured. This is because the center of a gravity G of the grasping portion 63 having an endoscope 61 mounted thereon is arranged substantially in the vertical line passing through the spherical center of the ball joint element 62 or center Ob of rotation of the ball joint element 62.

In the device disclosed in Jpn. Pat. Appln. KOKAI Publication No. 8-052158, U.S. Pat. No. 4,863,133, U.S. Pat. No. 5,170,790 or WO 95/10985, although the miniaturization is realized by the use of ball joint elements at the articulations, structural parts become unbalanced during movement. Therefore, the operator must eliminate this unbalance by himself by holding a structural part, for example, the grasping portion, so that the operability is degraded when requiring delicate operation.

In the device disclosed in Jpn. Pat. Appln. KOKAI Publication No. 6-113997 mentioned above, as the arm portion moves as a whole when moving a medical instrument, it can be held always under balanced condition, whereas the arm would interfere with an operator. In operation in cranial nerve surgery, particularly, as various devices used in an operation are concentrically arranged at an operation site in a lumen, there is a requirement for a miniaturization of the arm itself so as to be freely moved and held in a narrow moving space.

Figure 13C:
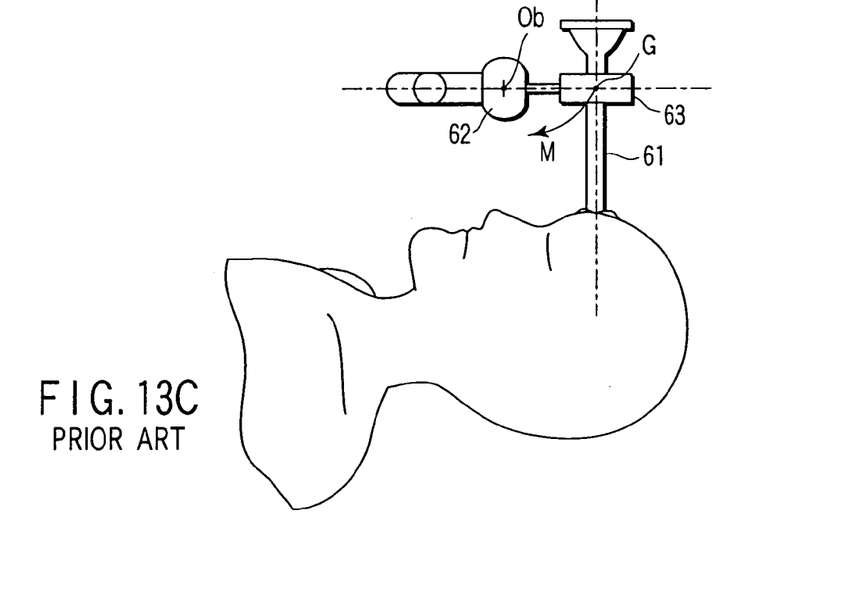
FIG. 13C is a view of a state using the endoscope holding portion of the medical instrument holding device of the prior art viewed from side.

In the device disclosed in Jpn. Pat. Appln. KOKAI Publication No. 2001-258903, moreover, when an operator actually uses the device in an operation, the insertion shaft of the endoscope 61 is used in the direction substantially coinciding with the direction of the gravity as shown in FIGS. 13B and 13C. Under the released condition of the ball joint element 62, however, the weight applied to the point G would fall in the direction M with respect to the point Ob. In other words, under this condition, an unbalanced state would occur and the operator would have to support by himself the weight of the endoscope 61 applying to the grasping portion 63, thereby resulting in degraded operability.

In the medical instrument holding devices of the prior art, as the arms in the proximity of operating position become bulky, they would interfere with the operation. Moreover, under the released condition of the arm, the operator has to move (or operate) the grasping portion and the medical instrument under an unbalanced condition that the center of gravity of the grasping portion and medical instrument thereon is shifted from the desired position, whereby the operability of the holding device is degraded. These problems would cause affection of an operator and complicate the work operation of the operator, resulting in a lower operation efficiency.

BRIEF SUMMARY OF THE INVENTION

Consequently, it is an object of the invention to provide a medical instrument holding device which provides a sufficient space to an operator around an operating position for a variety of operating procedures and is improved in operability with reduction of load applying to the operator particularly by balancing the weight of a grasping portion to be moved by the operator.

In order to accomplish the above object, the medical instrument holding device capable of holding a medical instrument having a long member to be inserted into the interior of a subject according to the invention comprises a grasping member having a longitudinal shaft and to be grasped by an operator, a holding portion provided on the grasping member and capable of holding the medical instrument so as to extend the long member of the medical instrument in a direction different from that of the longitudinal shaft of the grasping member, a ball joint element arranged above or below the axis of the longitudinal shaft of the grasping member and connected to the grasping portion, an arm portion having a movable free end, and a ball joint acceptant portion supporting the ball joint element provided on the free end of the arm portion in a ball joint manner.

The invention further provides the medical instrument holding device capable of holding a medical instrument having a long member to be inserted into the interior of a subject comprising a grasping member having a longitudinal shaft and to be grasped by an operator, a holding portion provided on the grasping member and capable of holding the medical instrument so as to extend the long member of the medical instrument in a direction different from that of the longitudinal shaft of the grasping member, an arm portion having a movable free end, a ball joint element provided on the free end of the arm portion, and a ball joint acceptant portion connected to the grasping member and arranged above or below of the axis of the longitudinal shaft of the grasping member to support the ball joint element in a ball joint manner.

DETAILED DESCRIPTION OF THE INVENTION

The embodiments of the invention will be explained in detail with reference to the drawings hereinafter.

Figure 1:
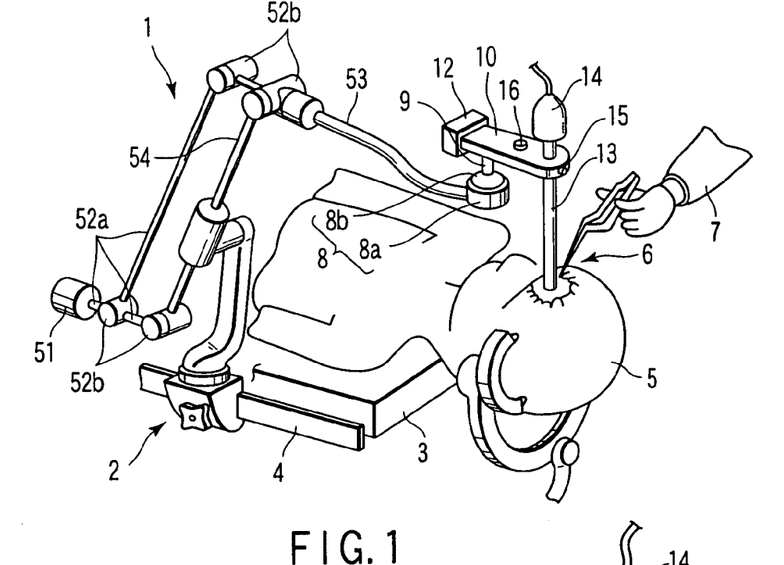
FIG. 1 is a perspective view illustrating the outline of the medical instrument holding device of the first embodiment according to the invention.
Figure 2:
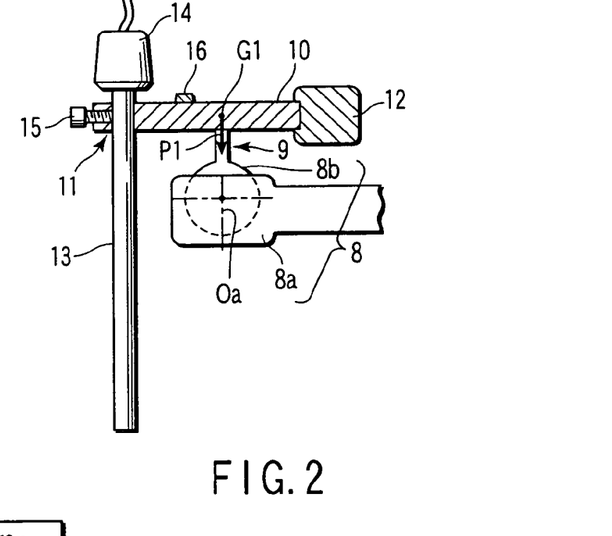
FIG. 2 is a view illustrating the construction of the endoscope holding portion of the medical instrument holding device of the first embodiment.
Figure 3:
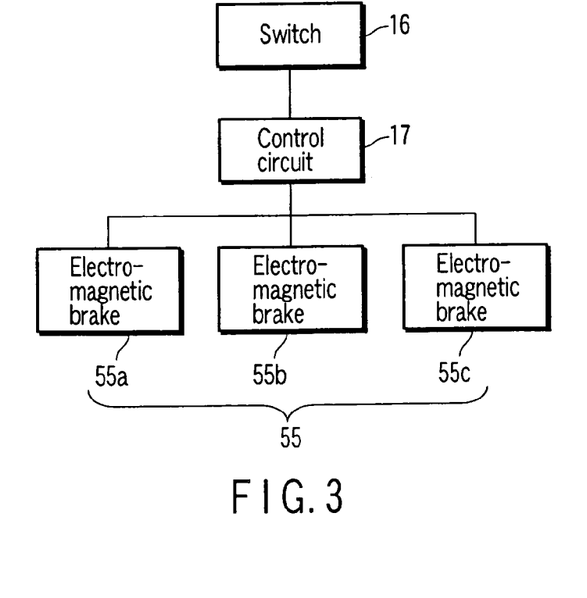
FIG. 3 is a block diagram of means for switching the medical instrument holding device of the first embodiment into fixed or released condition.
Figure 4:
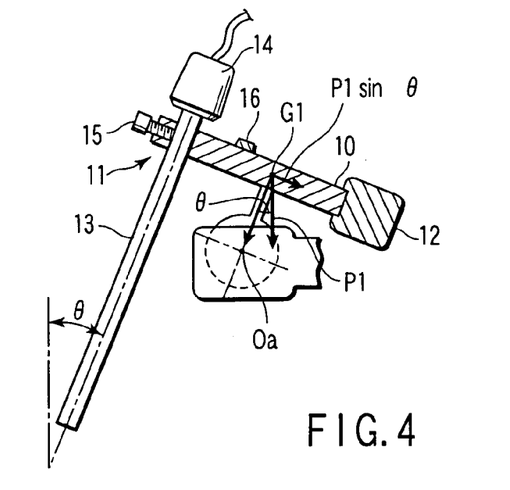
FIG. 4 is a view for explaining the operation of the endoscope holding portion of the medical instrument holding device of the first embodiment.

FIG. 1 illustrates the outline of the medical instrument holding device of the first embodiment of the invention in a used state. FIG. 2 shows the endoscope holding portion of the medical instrument holding device. FIG. 3 is a block diagram for realizing the state of the holding device being fixed or released. FIG. 4 is a view for explaining the operation of the endoscope holding portion in the first embodiment.

The medical instrument holding device (referred to herein as "holding device") 1 is slidably mounted with its proximal end 2 supporting the holding device main body on a side rail 4 of an operating table 3 in a similar manner to that in Jpn. Pat. Appln. KOKAI Publication No. 2001-258903 mentioned above. A patient 5 is lying face up on the operating table 3, while an operator 7 is treating an operation site through a lumen 6 of the patient opened at the surface of his head.

The proximal end 2 of the holding device 1 is provided with a support arm which extends vertically upward and is provided rotatably at its top end with a connecting portion on which a connecting arm 54 is supported. The connecting arm 54 and short and long link arms 52a are connected by articulations 52b to form a parallelogram link mechanism of which one link element is the connecting arm 54. The link arm 52a connected to the lower end of the connecting arm 54 is provided with a counter weight 51 at its distal end. On the other hand, the connecting arm 54 is provided at its upper end with an acceptant arm 53 horizontally extending. The counter weight 51 functions to cancel the force (weight) acting upon the acceptant arm 53 through the link mechanism.

In this construction, even if the parallelogram link is changed in its shape by moving the acceptant arm 53, the balance of force is kept by the counter weight 51, and the weight of the acceptant arm 53 is supported by the link mechanism. In addition, the counter weight 51 is so constructed that its weight can be adjusted to balance the total weight in consideration of weight of the acceptant arm 53 described later and a grasping portion 10 having a medical instrument mounted thereon. For example, the counter weight 51 may be slidable on the link arm 52a to adjust the weight (force) acting upon the link mechanism by the movement of the counter weight 51.

In other words, the total balance can be adjusted by suitably moving the counter weight 51 depending upon the weight of a medical instrument loaded on the holding device. Such a link mechanism is substantially similar in construction and functions and effects to the first parallel link mechanism disclosed in Jpn. Pat. Appln. KOKAI Publication No. 2001-258903 (FIG. 1), so that the link mechanism will not be described in further detail.

The acceptant arm 53 is provided at its distal end with a support portion 8 through which a grasping portion 10 is pivotally connected to the acceptant arm 53. The support portion 8 consists of a ball joint acceptant portion 8a, a ball joint element 8b supported by the ball joint acceptant portion 8a in a kinematic ball joint manner, and an electro-magnetic brakes 55 (not shown). The electro-magnetic brakes 55 are each provided in each articulation (ball joint element) as shown in FIG. 3. Such an electro-magnetic brake has a known construction capable of switching its fixed state and released state as disclosed, for example, in Jpn. Pat. Appln. KOKAI Publication No. 2001-258903.

As shown in FIG. 2, the ball joint element 8b is integrally provided with a shaft 9 which is fixed to the underside of the grasping portion 10 at the intermediate portion between longitudinal ends of the grasping portion 10. The grasping portion 10 is formed at its longitudinal end with a medical instrument fitting aperture 11 in parallel with the shaft 9 and at the other end with a counter weight 12 whose weight is W kg.

For example, an endoscope 13 (long member or elongated member) is inserted into the medical instrument fitting aperture 11 and fixed thereat by a set screw 15 provided in grasping portion 10. Connected to the proximal end of the endoscope is a television (TV) camera 14 which is connected through a cable (not shown) to a TV camera controller and further connected through a cable (not shown) to a monitor (not shown). The medical instrument fitting aperture 11 into which the endoscope 13 is fitted and the set screw 15 form a medical instrument holding mechanism in the embodiment. The following explanation will be described assuming that a medical instrument such as an endoscope has been loaded onto the grasping portion 10.

The grasping portion 10 is provided on its upper surface with a fixation release switch 16 connected through a cable (not shown) to a control circuit 17 as shown in FIG. 3. The control circuit 17 is connected through a cable (not shown) to the electro-magnetic brakes (not shown) as braking means in the embodiment provided at movable portions such as the articulations. The fixation release switch 16 may be of a type to be switched on only when being pushed or another type to be alternately switched on and off every time being pushed.

In this case, the total weight P1 (shown by an arrow in FIG. 2) of the medical instrument consisting of the endoscope 13 and the TV camera 14 and the grasping portion 10 (containing the counter weight 12) and further the center of a gravity G1 of these members are preferably arranged substantially in a vertical line passing through the center Oa of the ball joint element 8b. When a medical instrument is mounted on the grasping portion 10, this arrangement is adjusted by previously adjusting the weight W of the counter weight 12 so as to permit the total weight P1 to apply to the ball joint element 8b to be balanced.

The function in the first embodiment will be explained hereafter.

In general, the surgical operation starts from the surface of a patient and opens a lumen 6 of the body, whose direction is substantially in vertical direction. The endoscope 13 is inserted with its insertion portion into the lumen 6 and arranged in the proximity of an operation site. An operator 7 observes through the endoscope 13 images at the operation site produced on a monitor (not shown) by means of the camera 14. In order to change the observation field of view of the endoscope 13, the operator 7 grasps the grasping portion 10 and pushes the switch 16 to release the fixed condition of the electromagnetic brakes 55a to 55c arranged at the respective moving parts through the control circuit 17 at a time. While a plurality of brakes are released at a time by an operation of the switch in the embodiment, it will be apparent that a plurality of switches may be provided to release individual brakes separately by means of the control circuit 17 in such a case that it is desired to pivotally move an instrument by partly releasing the brakes depending on the mounted medical instrument.

By such a release, the ball joint acceptant portion 8a and the ball joint element 8b become movable about the center Oa. As the center of the gravity G1 is substantially in the vertical line passing through the center Oa of the ball joint element as described above, a situation will arise that the total weight P1 of the grasping portion 10 having the medical instrument (endoscope) mounted thereon is applied to the ball joint element 8b. Explaining further, when the operator 7 grasps the grasping portion 10, the load (weight) applying to the operator 7 is only a force for turning the grasping portion 10 about the center Oa. However, when the axis of insertion shaft of the endoscope is tilted, the load applying to the operator 7 grasping the grasping portion 10 may increase depending upon the angles. Such an increase in the load will be explained with reference to FIG. 4.

When the insertion axis of the endoscope 13 is tilted at an angle $\theta$ with respect to a vertical line, applied to the center of the gravity G1 is the weight P1 whose vector value is divided into two components, that is, the weight of $P1 \cdot \cos \theta$ applying to the ball joint element 8b and the weight of $P1 \cdot \sin \theta$ to be supported by the operator 7. Accordingly, when the center of the gravity G1 is in the vertical line passing through the center Oa, the angle $\theta$ is zero ($\theta=0$) so that the weight to be supported by the operator 7 becomes zero, and the weight to be supported by the operator 7 will increase or decrease according to the insertion angle $\theta$ of the endoscope by the factor of $P1 \cdot \sin \theta$.

In the recent surgical operation aiming at less invasive operation, however, what an operators may provide in the proximity of body surface is, for example, a bar hole of the order of 10 mm in diameter, whose direction is also approximately vertical. In reality, namely, there is typically little or no inclination of insertion axis of endoscope in surgical operation.

The link mechanism comprising the connecting arm 54, the link arms 52a, articulations 52b and the counter weight 51 invariably supports the weight of the grasping portion 10 having the acceptant arm 53 and the medical instrument loaded thereon. In the grasping portion 10 and the acceptant arm 53, moreover, since the center of the gravity G1 to which the total weight P1 of the grasping portion 10 is applied is substantially in the vertical line passing through the center Oa of the ball joint element 8b, the balance is already adjusted according to the invention in a manner that the total weight P1 of the grasping portion (including the medical instrument) is invariably applied to the ball joint element 8b. Therefore, the operator can easily move the grasping portion without being subjected to the weight of the grasping portion 10.

According to the first embodiment of the invention described above, the holding device is simple in construction and inexpensive to manufacture because the grasping portion consists of the counter weight and the medical instrument fitting aperture so as to be very simple construction. This grasping portion enables attaching various medical instruments having a general insertion shaft additionally at a later time. Although the holding device of the embodiment has been explained using an endoscope as a medical instrument to be held by way of example, the invention of course is not limited thereto and other instruments used in surgical operation such as treating devices may be held by the holding device according to the invention.

In the embodiment, moreover, the electro-magnetic brakes are used as means for fixing the movable portions of the holding device, but it is not limited to such brakes. Use of brakes utilizing pressurized fluid as described in the U.S. Pat. No. 5,170,790 is within the scope of the present invention. Although the link mechanism for balancing the weight is used in the embodiment, it is to be understood that the invention is not limited to the use of such a mechanism and, for example, one fixed bar provided at one end with a ball joint element may bring about the equivalent effect.

The medical instrument holding device of the second embodiment of the invention will be explained thereafter.

Figure 5:
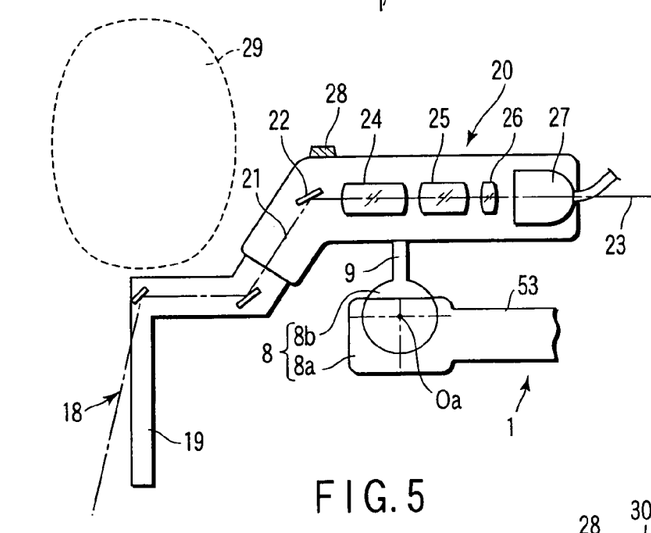
FIG. 5 is a view illustrating in section the construction of the grasping portion including an endoscope in the medical instrument holding device of the second embodiment.

FIG. 5 illustrates in cross-section a grasping portion including an endoscope of the holding device.

The second embodiment has a construction equivalent to those of the parallelogram link mechanism (consisting of the connecting arm, the link arms, the articulations and the counter weight) connected to the acceptant arm in the first embodiment. In the second embodiment, a connecting arm 54 is supported by a connecting portion which is provided with a connecting arm and a support arm pivotally movable. Such a construction is applicable to the mechanism including the braking portions (pushing levers) by pushing levers as shown in FIG. 6 in Jpn. Pat. Appln. KOKAI Publication No. 2001-258903 mentioned above. In the articulations, moreover, electro-magnetic brakes functioning as braking means are provided.

Although in the first embodiment a medical instrument such as an endoscope is detachably mounted on the grasping portion, in the second embodiment a photographing optical system is provided in a grasping portion and the forward end of a shaft extending from a ball joint element is modified. Moreover, corresponding components in the second embodiment are identified by identical reference numerals used in the first embodiment.

Connected to the longitudinal end of the grasping portion 20 is the proximal end of an endoscope, and further connected to the endoscope is an L crank-shaped insertion shaft 19. The grasping portion 20 is provided on its lower side (on the extending side of the insertion shaft 19) with a shaft 9 having a ball joint element 8b. The ball joint element 8b is supported by a ball joint acceptant portion 8a provided on the forward end of an acceptant arm 53 in a kinematic ball joint manner.

The insertion shaft 19 is provided with reflector mirrors each at a corner of the L crank shape, and when the insertion shaft 19 is inserted into a lumen of a body, luminous flux (image in the endoscope) at the operation site obtained at the forward end of the insertion shaft is reflected by the mirrors to introduce the flux to the proximal end of the endoscope. In the grasping portion 20 there are provided mirrors 22, a focus optical system 24, a zoom optical system 25 and an imagery optical system 26 and further a TV camera 27 at a location of image formation by the imagery optical system 26.

In this construction, the luminous flux incident from the forward end of the insertion shaft 19 in the axial direction (substantially vertical direction) is conducted to the proximal end of the endoscope 18. The luminous flux 21 projected from the proximal end is reflected at the mirrors 22 so as to advance into the focus optical system 24. Further, after the luminous flux 21 has been optically processed in the zoom optical system 25 and the imagery optical system 26, the luminous flux 21 is imaged on a semiconductor image pick-up device consisting of a charge coupled device (CCD) and the like in the TV camera and photographed as pictorial image by photoelectric transformation. The pictorial images photographed by the TV camera are displayed on a monitor (not shown) similar to that in the first embodiment.

Moreover, the grasping portion 20 is provided on its upper surface with a switch 28 functioning as inputting means constructed similarly to the fixation release switch 16 in the first embodiment. The switch 28 is operated by an operator for inputting the instruction for fixing or releasing brakes such as electro-magnetic brakes (not shown) provided in respective articulations of the device. The switch 28 is connected through a cable (not shown) to a control circuit similar to that shown in FIG. 3, and the fixation or release of the brakes such as electro-magnetic brakes is instructed by the control circuit. Further, the center of gravity of the grasping portion 20 having the endoscope 18 mounted thereon is preferably arranged in the vertical line passing through the point Oa.

In such a construction, when the operator actuates the switch 28, the fixation of the electro-magnetic brakes (not shown) is released. By the release of the brakes, the articulation of the link mechanism and the support portion 8 (ball joint element) come under free condition, thereby enabling the articulations and the support portion 8 to be moved by the operator. At this time, as described in the first embodiment, the total weight of the grasping portion 20 having the acceptant arm 53 and the medical instrument mounted thereon is supported by the link mechanism by adjusting the counter weight. Moreover, since the total weight of the grasping portion 20 is substantially in the vertical line passing through the center Oa of the ball joint element 8b, the balance is adjusted so that the total weight of the grasping portion 20 may be applied to the ball joint element 8b of the acceptant arm 53. Therefore, the operator can easily move the grasping portion without being suffered from the weight of the. grasping portion 10.

The construction of the embodiment achieves a particular advantage of more weight saving by using the optical systems instead of the counter weight in the first embodiment. However, the insertion shaft 19 to be mounted is limited to those of a weight previously determined to be balanced. Therefore, the balance about the center Oa of the ball joint element (weight of a structure consisting of the grasping portion and the endoscope) is more improved, resulting in an improved operability. Moreover, the optical path of the optical systems is bent at plural portions to generate a space 29 which provides a sufficient space to the operator even when using together with a microscope for surgical operation.

The medical instrument holding device of the third embodiment according to the invention will be explained hereinafter.

Figure 6:
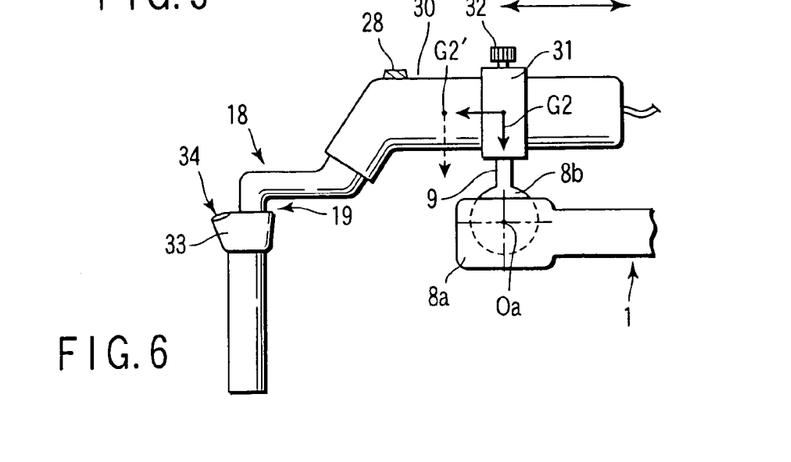
FIG. 6 is a view illustrating in section the construction of the grasping portion including an endoscope in the medical instrument holding device of the third embodiment.

FIG. 6 illustrates in section a grasping portion including an endoscope in the medical instrument holding device of the third embodiment. In the third embodiment, the grasping portion and the insertion shaft in the second embodiment are modified. Other than these features are substantially similar to those of the first and second embodiments, and components similar to those are identified by identical reference numerals and will not be described in further detail.

The grasping portion 30 is fitted in a ring member 31 and fixed thereto by a set screw 32. By loosening the set screw 32, the grasping portion 30 is moved slidably in the directions shown by an orienting arrow in the drawing. The ring member 31 is provided at its lower portion with a ball joint element 8b by means of a shaft 9. Mounted on the end of the grasping portion 30 is an endoscope 18 whose insertion shaft 19 is provided with a sheath inserted and fitted thereto. The sheath 33 has a lumen into which a treating device is inserted.

In this construction, the center of a gravity G2 of the total weight of the grasping portion 30 including the endoscope 18 and the insertion shaft 19 and the ring member 31 is in the vertical line passing through the spherical center Oa of the ball joint element 8a. When the sheath 33 is secured to the endoscope 18 by the operator 7, the total weight will be increased by the weight of the sheath 33, so that the center of gravity is shifted to the point G2' onto the left, thereby causing an unbalance. Then, the set screw 32 is loosened and the grasping portion 30 is moved toward the right hand in the drawing so that the center of gravity (not shown) described above is brought into the position substantially in the vertical line passing through the center Oa. Thereafter, the set screw is tightened to fix the grasping portion 30 to the ring member 31.

As can be seen from the above, the medical instrument holding device of the third embodiment has a particular effect that even if a sheath or the like is added to the endoscope or the balance is changed by newly added member on the forward side of the ball joint element, the center of gravity of the structure can be adjusted relative to the center position of the ball joint element depending upon the resulting unbalance. As a result, even if the balance of the peripheral portions of the endoscope is changed according to proceeding of operation, the operability is not degraded with the aid of the adjustment.

The medical instrument holding device of the fourth embodiment of the invention will be explained hereafter.

Figures 7, 8, 9, 10:
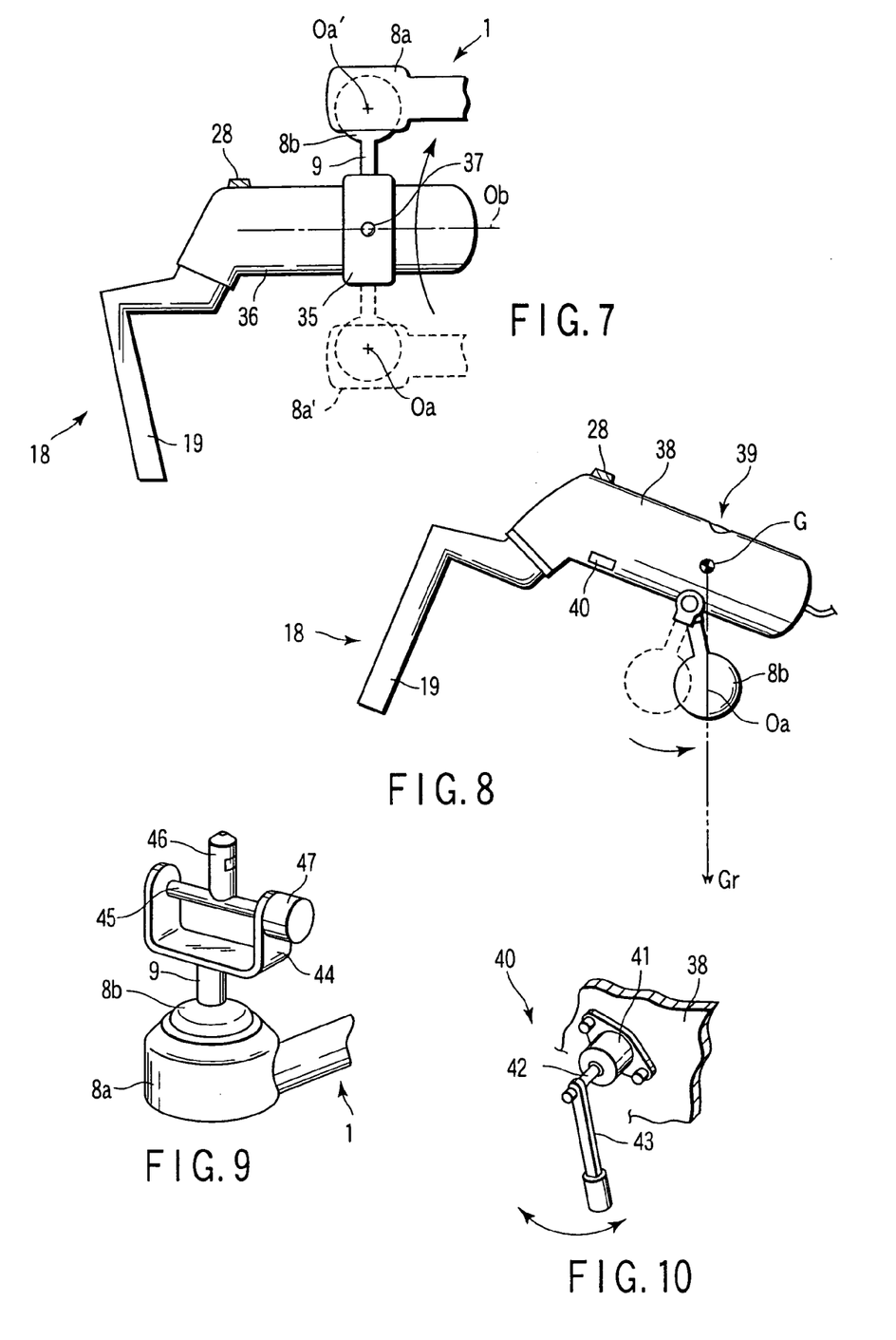
FIG. 7 is a view illustrating in section the construction of the grasping portion including an endoscope in the medical instrument holding device of the fourth embodiment.
FIG. 8 is a view illustrating in section the construction of the grasping portion including an endoscope in the medical instrument holding device of the fifth embodiment.
FIG. 9 is a view illustrating the outline of a ball joint element mounted on the grasping portion in the medical instrument holding device of the fifth embodiment.
FIG. 10 is a view illustrating an example of means for detecting an attitude of the grasping means of the medical instrument holding device of the fifth embodiment.

FIG. 7 illustrates in section a grasping portion including an endoscope in the medical instrument holding device of the fourth embodiment. In the fourth embodiment, the grasping portion and the insertion shaft in the second embodiment are modified. Other than these features are substantially similar to those of the first and second embodiments, and components similar to those are identified by identical reference numerals and will not be described in further detail.

The grasping portion 36 is fitted in a ring member 35 and fixed thereto by a set screw 37. By loosening the set screw 37, the grasping portion 36 can be rotatable as shown by an arrow in the drawing. A ball joint element 8b is integrally fixed through a shaft 9 to the ring member 35. It is desirable that the center point Oa' is substantially in the vertical line passing through the center of gravity of the structure consisting of the grasping portion 36 and the endoscope 18. Secured to the end of the grasping portion 36 is the endoscope 18 having an insertion shaft 19.

According to such a construction, when the operator desires to have a wider space below the grasping portion 36 in accordance with the procedure of operation, the set screw 37 is loosened and the ring member 35 is then rotated from the position shown in broken lines in the drawing to the position in solid lines, that is, from below to above the grasping portion. The set screw 37 is then tightened to fix the grasping portion 36 to the ring member 35. Now, the center point Oa' is substantially in the vertical line passing through the center of gravity of the structure consisting of the grasping portion 36 and the endoscope 18. Therefore, even if the ball element 8b and the ball joint acceptant portion 8a come under free condition, there is no movement of the grasping member 36 due to its own weight.

According to the above construction, in the event that the operator desires a space still more above or below the grasping portion or the ball joint element (ball joint acceptant portion) interferes with the space, the position of the ball joint element can be varied which is particular advantage. As a result, a sufficient space can be given to the operator by moving the ball joint element to the opposite side in accordance with circumstances such as that a patient or microscope for operation occupies the space required for the operation.

The medical instrument holding device of the fifth embodiment of the invention will be explained.

Figure 11:
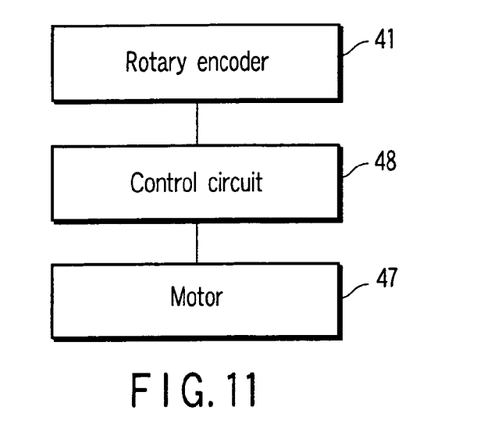
FIG. 11 is a block diagram of the support portion of the medical instrument holding device of the fifth embodiment.
Figure 12:
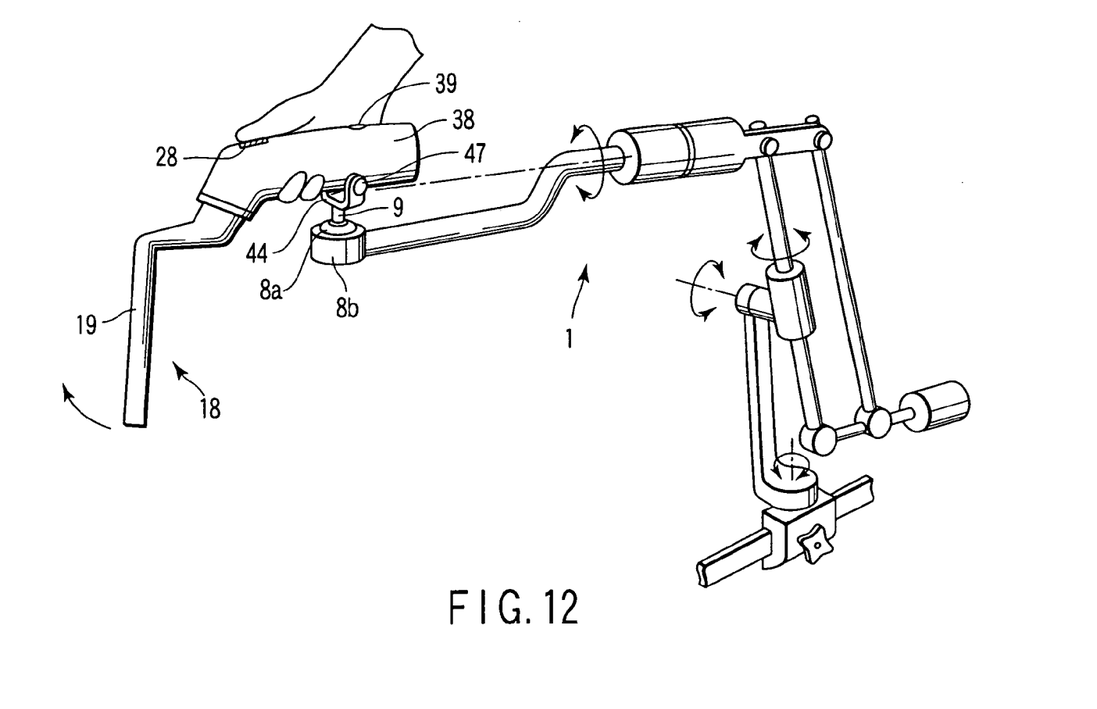
FIG. 12 is a view illustrating the entire outline of the medical instrument holding device of the fifth embodiment.

FIG. 8 illustrates in section a grasping portion including an endoscope in the medical instrument holding device of the fifth embodiment. In the fifth embodiment, the grasping portion and the insertion shaft in the second embodiment are modified. Other than these features are substantially similar to those of the first and second embodiments, and components similar to those are identified by identical reference numerals and will not be described in further detail. FIG. 9 illustrates the outline of a ball joint element 8b secured to the grasping portion and FIG. 10 shows an exemplary means for detecting an attitude of the grasping portion. FIG. 11 illustrates a block diagram of the support portion and FIG. 12 shows an entire outline of the medical instrument holding device.

The center of gravity of the grasping portion 38 having an endoscope 18 mounted thereon is shown by a point G in the drawing. The grasping portion 38 is provided in its upper and lower positions with connecting apertures 39, respectively in a manner such that these connecting apertures 39 are positions in the vertical line passing through the center of the gravity G of the grasping portion 38 when the insertion shaft 19 of an endoscope 18 assumes in the vertical position. The grasping portion 38 is provided therein with an attitude detector 40 for detecting an attitude of the grasping portion 38. The attitude detector 40 comprises a rotary encoder 41 and a weight 43 mounted on a rotating shaft 42 of the rotary encoder 41.

Fixed to the grasping portion 38 is a shaft 9 provided with a U-shaped member 44 mounted on the shaft 9. A shaft 45 is supported or journalled at both ends by the U-shaped member 44 and is provided at the mid portion with a connecting bar 46. One end of the supported shaft 45 is connected to a rotating shaft of a motor 47 so that the shaft 45 is rotationally driven by the motor 47.

The connecting bar 46 is inserted into one of the connecting apertures 39 of the grasping portion 38 and fixed to the grasping portion 38 by means of a screw (not shown). The rotary encoder 41 is connected through a cable (not shown) to a control circuit 48. The motor 47 also is connected through a cable (not shown) to the control circuit 48 for controlling its driving movement.

In such a construction, when the insertion shaft 19 of the endoscope 18 is tilted by an operator as shown in FIG. 12, the weight 43 tends to pivotally move into a vertical position by its own weight. Such a change in orientation of the insertion shaft 19 is detected as a rotated angle of the rotating shaft 42. The control circuit 48 receives the detected result from the rotary encoder 41 and energizes the motor 47 so that the center Oa of the ball joint element 8b may be positioned in the vertical line passing through the center point G. If the ball joint element 8b and the ball joint acceptant portion 8a form obstacles for the operator, the screw 49 is loosened by the operator and the connecting bar 46 inserted in the connecting aperture 39 of the grasping portion 38 is removed. The connecting bar 46 is then inserted into another connecting aperture 39 and fixed thereto by tightening a screw 49.

In addition to the effects of the fourth embodiment described above, the device of the fifth embodiment has a particular effect that the position of the ball joint can be automatically adjusted relative to the position of center of a gravity G corresponding to the attitude of the endoscope to provide much better operability. Moreover, the device has a further particular effect that when the grasping portion is removed from the holding device, the endoscope can be used independently.

In the actual use of the endoscope, moreover, the center of a gravity G1 of the weight P1 of the grasping portion having the endoscope mounted thereon is arranged in the vertical line passing through the center point Oa of the ball joint element and this balance is maintained when being operated (moved), so that the weight P1 is not loaded onto the operator to improve the operability of the holding device which is the best effect.

In FIG. 2, moreover, even if the point G1 does not coincides with the vertical line passing through the point Oa, the operator is required only a turning force about the center Oa of the ball joint, as can be seen from the component obtained by dividing the vector value of the weight P1. Therefore, the holding device is clearly different from the medical instrument holding device of the prior art in that an operator has to support all the weight P1.

As can be seen from the above detailed explanation, the present invention can provide an improved medical instrument holding device superior in operability, which provides a sufficient space around the operating position for a wide variety of operating formulas and particularly enables the weight of the grasping portion moved by an operator to be remarkably reduced by balancing.

What is claimed is:

1. A medical instrument holding device capable of holding a medical instrument having a long member to be inserted into the interior of a subject, comprising:
    a grasping member having a longitudinal shaft and to be grasped by an operator,
    a holding portion provided on the grasping member and capable of holding the medical instrument so as to extend the long member in a direction different from that of the longitudinal shaft of the grasping member,
    a ball joint element arranged above or below the axis of the longitudinal shaft of the grasping member and connected to the grasping member,
    an arm portion having a movable free end,
    a ball joint acceptant portion supporting the ball joint element provided on the free end of the arm portion in a ball joint manner, and
    a shaft member which connects a structure comprising the medical instrument and the grasping member to the ball joint element, the shaft member connecting the ball joint element and the structure on a substantially straight line connecting between a center of gravity G of the structure and a position P of a ball center of the ball joint element, wherein the substantially straight line connecting between the center of gravity G of the structure and the position P of the ball center of the ball joint element extends in a direction different from the longitudinal shaft of the grasping member.

2. The medical instrument holding device according to claim 1, wherein the arm portion comprises:
    a fixed portion fixed to a floor or operating table,
    a connecting arm connected to the fixed portion,
    an acceptant arm provided with the ball joint element or the ball joint acceptant portion,
    a plurality of link arms connected to the connecting arm and the acceptant arm via articulations, and
    a counter weight provided on at least one of the plurality of link arms so that the balance of moment of rotation produced at the ball joint element or the ball joint acceptant portion provided on the acceptant arm is maintained when the medical instrument is held on the holding portion.

3. The medical instrument holding device according to claim 2, wherein the device further comprises a braking portion provided in the articulations of the arm portion and between the ball joint element and the ball joint acceptant portion to switch the articulations as well as the ball joint element and the ball joint acceptant portion into a fixed condition and a free condition.

4. The medical instrument holding device according to claim 3, wherein the braking portion comprises electromagnetic brakes and a controller which controls the electromagnetic brakes, and
    the grasping member is provided with a switch which instructs the fixed condition or free condition of the braking portion to the controller.

5. The medical instrument holding device according to claim 1, wherein an inserting shaft portion having an L-shaped crank form is connected to the grasping member to provide a space in the longitudinal direction.

6. The medical instrument holding device according to claim 1, wherein the longitudinal direction is substantially at right angles to an insertion direction which coincides with an axial direction of the long member.

7. A medical instrument holding device capable of holding a medical instrument having a long member to be inserted into the interior of a subject, comprising:
    a grasping member having a longitudinal shaft and to be grasped by an operator,
    a holding portion provided on the grasping member and capable of holding the medical instrument so as to extend the long member in a direction different from that of the longitudinal shaft of the grasping member,
    a ball joint element arranged above or below the axis of the longitudinal shaft of the grasping member and connected to the grasping member,
    an arm portion having a movable free end,
    a ball joint acceptant portion supporting the ball joint element provided on the free end of the arm portion in a ball joint manner,
    an attitude detector provided in the grasping member and comprising a pointing portion pointing the vertical direction and a detecting portion rotatably supporting the pointing portion to detect a tilted angle,
    a U-shaped member pivotally supporting the grasping member,
    a shaft journalled by the U-shaped member and provided with a connecting bar which is detachably fitted in the grasping member,
    a motor provided at one end of the shaft to rotate the shaft, and
    a control means for controlling the rotation of the motor on the basis of detected results by the attitude detector.

8. A medical instrument holding device capable of holding various medical instruments having a long member to be inserted into the interior of a subject, comprising:
    a grasping member having a longitudinal shaft, whose center of gravity is changed by movement of a grasping position, a holding portion provided on the grasping member and capable of exchangeably holding the various medical instruments, along the longitudinal shaft, so as to extend the long member in a direction different from that of the longitudinal shaft of the grasping member, a ball joint element arranged above or below the axis of the longitudinal shaft of the grasping member and connected to the grasping member, an arm portion having a movable free end, a ball joint acceptant portion supporting the ball joint element provided on the free end of the arm portion in a ball joint manner, and a shaft member which connects a structure constituted of a medical instrument held by the holding portion and the grasping member to the ball joint element, wherein when the medical instrument held by the holding portion is exchanged for another medical instrument, the shaft member connects a structure comprising said another medical instrument and the grasping member to the ball joint element along a line connecting a gravity G of a structure constituted of said another medical instrument and the grasping member, whose grasping position has been moved to adjust the center of gravity, to the position P of the ball center of the ball joint element, and the line is substantially parallel to an insertion direction which coincides with an axial direction of the long member.

9. An endoscope holding device capable of holding an insertion portion for an endoscope having a long member to be inserted into the interior of a subject, comprising:

a first optical system contained in the insertion portion a guide an optical image of an object of observation, a grasping member which is connected to the insertion portion, contains an image pickup element and a second optical system that forms an optical image guided from the first optical system on the image pickup element, has a longitudinal shaft and is to be grasped by an operator, a ball joint element arranged above or below the axis of the longitudinal shaft of the grasping member and connected to the grasping member, an arm portion having a movable free end, a ball joint acceptant portion supporting the ball joint element provided on the free end of the arm portion in a ball joint manner, and a shaft member which connects a structure comprising the insertion portion for an endoscope and the grasping member to the bail joint element, the shaft member connecting the ball joint element and the structure on a substantially straight line connecting between a center of gravity G of the structure and a position P of a ball center of the ball joint element.

10. A medical instrument holding device comprising:

a medical instrument having a long member to be inserted into the interior of a subject and a grasping member having a longitudinal shaft and to be grasped by an operator, the long member extending in a direction different from that of the longitudinal shaft of the grasping member, a ball joint element arranged above or below the axis of the longitudinal shaft of the grasping member, an arm portion having a movable free end, a ball joint acceptant portion supporting the ball joint element provided on the free end of the arm portion in a ball joint manner, and a shaft member which connects the medical instrument to the ball joint element, the shaft member connecting the ball joint element and the medical instrument on a substantially straight line connecting between a center of gravity G of the medical instrument and a position P of a ball center of the ball joint element, wherein the substantially straight line connecting between the center of gravity G and the position P of the ball center extends in a direction different from the longitudinal shaft of the grasping member.

11. The medical instrument holding device according to claim 10, wherein the arm portion comprises:

a fixed portion fixed to a floor or operating table, a connecting arm connected to the fixed portion, an acceptant arm provided with the ball joint element or the ball joint acceptant portion, a plurality of link arms connected to the connecting arm and the acceptant arm via articulations, and a counter weight provided on at least one of the plurality of link arms so that the balance of moment of rotation produced at the ball joint element or the ball joint acceptant portion provided on the acceptant arm is maintained when the medical instrument is connected to the ball joint element.

12. The medical instrument holding device according to claim 11, wherein the device further comprises a braking portion provided in the articulations of the arm portion and between the ball joint element and the ball joint acceptant portion to switch the articulations as well as the ball joint element and the ball joint acceptant portion into a fixed condition and a free condition.

13. The medical instrument holding device according to claim 12, wherein the braking portion comprises electromagnetic brakes and a controller which controls the electromagnetic brakes, and the grasping member is provided with a switch which instructs the fixed condition or free condition of the braking portion to the controller.

14. The medical instrument holding device according to claim 10, further comprising a connecting member which is capable of moving the grasping member in the longitudinal direction of the grasping member.

15. The medical instrument holding device according to claim 10, further comprising:

an attitude detector provided in the grasping member and comprising a pointing portion pointing the vertical direction and a detecting portion rotatably supporting the pointing portion to detect a tilted angle, a U-shaped member pivotally supporting the grasping member, a shaft journalled by the U-shaped member and provided with a connecting bar which is detachably fitted in the grasping member, a motor provided at one end of the shaft to rotate the shaft, and a control means for controlling the rotation of the motor on the basis of detected results by the attitude detector.

16. The medical instrument holding device according to claim 10, wherein the longitudinal direction is substantially at right angles to an insertion direction which coincides with an axial direction of the long member.

17. The medical instrument holding device according to claim 10, wherein a line connecting a gravity G of a structure comprising the medical instrument and the grasping member to the position P of the ball center of the ball joint element is substantially parallel to an insertion direction which coincides with an axial direction of the long member.

* * * * *